: US006835831B2

United States Patent
Hirth

(10) Patent No.: US 6,835,831 B2
(45) Date of Patent: Dec. 28, 2004

(54) DIASTEREOSELECTIVE SYNTHESIS OF UDP-GLUCOSE: N-ACYLSPHINGOSINE GLUCOSYLTRANSFERASE INHIBITORS

(75) Inventor: Bradford H. Hirth, Littleton, MA (US)

(73) Assignee: Genzyme Corporation, Cambridge, MA (US)

(*) Notice: Subject to any disclaimer, the term of this patent is extended or adjusted under 35 U.S.C. 154(b) by 3 days.

(21) Appl. No.: 10/305,787

(22) Filed: Nov. 26, 2002

(65) Prior Publication Data

US 2003/0153768 A1 Aug. 14, 2003

Related U.S. Application Data

(60) Provisional application No. 60/333,392, filed on Nov. 26, 2001.

(51) Int. Cl.[7] ............... C07D 223/04; C07D 417/00; C07D 419/00; C07D 413/00; C07D 401/00
(52) U.S. Cl. ............... 540/607; 544/60; 544/137; 544/369; 546/209; 546/271.4; 548/239; 548/530; 548/953; 554/55; 564/414
(58) Field of Search ............... 540/607; 544/60, 544/137, 369; 546/209, 271.4; 548/239, 530, 953; 554/55; 564/414

(56) References Cited

U.S. PATENT DOCUMENTS

| 4,695,580 A | 9/1987 | Ohashi et al. |
| 6,030,995 A | 2/2000 | Shayman et al. |

FOREIGN PATENT DOCUMENTS

| DE | 2 218 009 | 11/1973 |
| DE | 28 42 639 A1 | 4/1980 |
| EP | 0 782 992 A1 | 7/1997 |
| EP | 1 106 609 A2 | 6/2001 |
| JP | 53-053615 | * 5/1978 |
| JP | 02 053781 | 2/1990 |

OTHER PUBLICATIONS

Soloshonok, V. A., et al., "Gold(I)–Catalyzed Asymmetric Aldol Reactions of Isocyanoacetic Acid Derivatives with Fluoroaryl Aldehydes," *Tetrahedron*, 52(1):245–254 (1996).

(List continued on next page.)

*Primary Examiner*—Richard L. Raymond
*Assistant Examiner*—Zachary C. Tucker
(74) *Attorney, Agent, or Firm*—Hamilton, Brook, Smith & Reynolds, P.C.

(57) ABSTRACT

Disclosed is a method of preparing a composition comprising a compound represented Structural Formula (I):

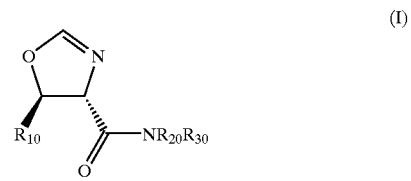

(I)

The method comprises the step of reacting an aldehyde compound $R_{10}CHO$ with an isonitrile compound represented by Structural Formula (II):

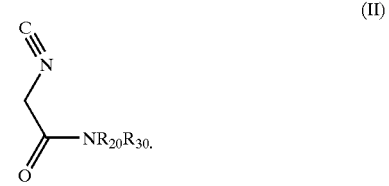

(II)

33 Claims, 1 Drawing Sheet

OTHER PUBLICATIONS

Ito, Y., et al., "Asymmetric Aldol Reaction of α–Isocyanoacetamides with Aldehydes Catalyzed by a Chiral Ferrocenylphosphine–Gold(I) Complex," *Tetrahedron Letters*, 29(48): 6321–6324 (1988).

Soloshonok, V. A., et al., "Gold(I)–Catalyzed Asymmetric Aldol Reactions of Fluorinated Benzaldehydes with an α–Isocyanoacetamide," *Tetrahedron: Asymmetry* 5(6) : 1091–1094, 1994.

Soloshonok, V. A., et al., "Gold (I)–Catalyzed Asymmetric Aldol Reactions of Isocyanacetic Acid Derivatives with Fluoroaryl Aldehydes," *Tetrahedron* 52(1) :245–254, 1996.

Ito, Y., et al., "Asymmetric Aldol Reaction of α–Ketoesters with Isocyanoacetate and Isocyanoacetamide Catalyzed by a Chiral Ferrocenylphosphine–Gold(I) Complex," *Tetrahedron Letters* 30(35) :4681–4684, 1989.

Ozaki, Y., et al., "An Improved Stereoselective Synthesis of threo–β–Hydroxyamino Acids," *Synthesis* 1:216–217, 1979.

Kurosawa, M., et al., "C–Labeling of a Novel Atypical β–Adrenoceptor Agonist, SM–11044," *J Labelled Compounds Radiopharmaceuticals* 37(3) :285–297, 1996.

Soloshonok, V. A., et al., "Transition Metal/Base–Catalyzed Aldol Reactions of Isocyanoacetic Acid Derivatives with Prochiral Ketones, a Straightforward β,β–Distributed–β–ydroxy–a–amino Acids. Scope and Limitations," J Organic Chemistry 62(11):3470–3479, 1997.

* cited by examiner

DIASTEREOSELECTIVE SYNTHESIS OF UDP-GLUCOSE: N-ACYLSPHINGOSINE GLUCOSYLTRANSFERASE INHIBITORS

RELATED APPLICATION

This application claims the benefit of U.S. Provisional Application No. 60/333,392, filed Nov. 26, 2001. The entire teachings of the above application are incorporated herein by reference.

BACKGROUND OF THE INVENTION

Glycosphingolipids (GSLs) are a class of naturally occurring compounds which have a multitude of biological functions, including the ability to promote cell growth, cell differentiation, adhesion between cells or between cells and matrix proteins, binding of microorganisms and viruses to cells, and metastasis of tumor cells. GSLs are derived from glucosylceramide (GlcCer), which is produced from ceramide and UDP-glucose by the enzyme UDP-glucose: N-acylsphingosine glucosyltransferase (GlcCer synthase). The structure of ceramide is shown below:

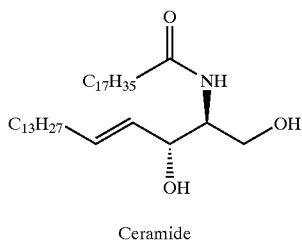

Ceramide

The accumulation of GSLs has been linked to a number of diseases, including Tay-Sachs, Gaucher's, and Fabry diseases (see, for example, U.S. Pat. No. 6,051,598). GSLs have also been linked to certain cancers. For example, it has been found that certain GSLs occur only in tumors or at abnormally high concentrations in tumors; exert marked stimulatory or inhibitory actions on tumor growth when added to tumor cells in culture media; and inhibit the body's normal immunodefense system when shed by tumors into the surrounding extracellular fluid. The composition of a tumor's GSLs changes as the tumors become increasingly malignant and antibodies to certain GSLs inhibit the growth of tumors.

Compounds which inhibit GlcCer synthase can lower GSL concentrations and have been reported to be useful for treating subjects with one of the aforementioned diseases. A number of potent inhibitors of GlcCer, referred to herein as "ceramide-like compounds", are disclosed in U.S. Pat. Nos. 6,051,598, 5,952,370, 5,945,442, 5,916,911 and 6,030,995. The term "ceramide-like compounds" refers to analogs of ceramide in which: 1) the primary alcohol is replaced with a substituted amino group; and 2) the alkenyl group ($C_{13}H_{27}$—CH=CH—) is replaced with an aryl group, preferably phenyl or substituted phenyl. An enantiomer of a ceramide-like compound is referred to here as a "ceramide-like enantiomer". The corresponding N-deacylated compounds are referred to as "sphingosine-like compounds".

Unfortunately, known methods of preparing ceramide-like compounds are poorly suited for manufacturing on an industrial scale. Because of the two chiral centers, most known syntheses generate four diastereoisomers, resulting in the need to separate diastereomers by chromatography. Unfortunately, chromatography is generally poorly suited for large scale preparations. Thus, there is a critical need for diastereoselective syntheses of ceramide-like compounds which are more economical and involve fewer steps than known syntheses.

SUMMARY OF THE INVENTION

Reported herein is an efficient, highly diastereoselective synthesis of ceramide-like compounds. This synthesis of ceramide-like compounds involves only five steps from known compounds. For example, the ceramide-like compound designated "(6)" in FIG. 1 was produced in a diastereomeric excess of at least 99.3% and an overall yield of 16% (see Examples 1–5). Based on this discovery, novel reactions which can be used in a total synthesis of ceramide-like compounds and novel intermediates prepared by said reactions are disclosed herein.

One embodiment of the present invention is a method of preparing a first composition comprising a compound represented Structural Formula (I):

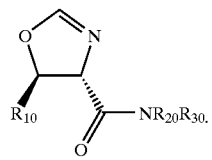

(I)

The method comprises the step of reacting an aldehyde compound $R_{10}CHO$ with an isonitrile compound represented by Structural Formula (II):

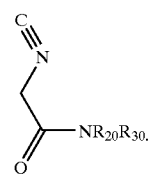

(II)

The reaction is carried out in the absence of a chiral inducing agent.

Another embodiment of the present invention is a method of preparing a second composition comprising a compound represented by Structural Formula (III):

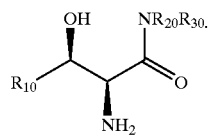

(III)

The second composition is prepared by hydrolyzing the oxazoline group in the compound represented by Structural Formula (I).

Another embodiment of the present invention is a method of preparing a third composition comprising a compound represented by Structural Formula (IV):

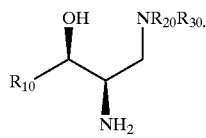

(IV)

The third composition is prepared by reacting the amide group in the compound represented by Structural Formula (III) with an amide reducing agent.

Another embodiment of the present invention is a method of preparing a fourth composition comprising a ceramide-like compound represented by Structural Formula (V):

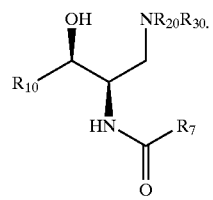

(V)

The fourth composition is prepared by acylating the free primary amine groups in the compound represented by Structural Formula (IV).

In Structural Formulas (I)–(V), $R_7$ is an aliphatic group, preferably a C1–C30 straight chained alkyl or alkenyl group, more preferably a C8–C18 straight chained alkyl group; $R_{10}$ is a substituted or unsubstituted aromatic group; and $R_{20}$ and $R_{30}$ are independently —H, a substituted or unsubstituted aliphatic group or, taken together with the nitrogen atom to which they are bonded, are a substituted or unsubstituted non-aromatic heterocyclic ring. Preferably, $R_{10}$ is not 3-pyridyl, phenyl or 4-nitrophenyl when $R_{20}$ and $R_{30}$ are both —H.

Another embodiment of the present invention is a compound represented by Structural Formula (VI):

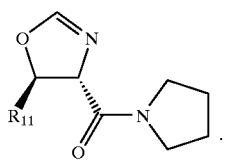

(VI)

$R_{11}$ is a substituted or unsubstituted phenyl group. Examples of suitable substituents for the phenyl group represented by $R_{11}$ include —OCH$_2$O—, —OCH$_2$CH$_2$O—, halo, —O(lower alkyl), lower alkyl thiol, —OH, —O(phenyl), —O—CH$_2$-(phenyl), lower alkyl, amino, lower alkyl amino and lower dialkyl amino. In a preferred embodiment, the compound is Intermediate (3) depicted in FIG 1.

Yet another embodiment of the present invention is a compound represented by Structural Formula (VII):

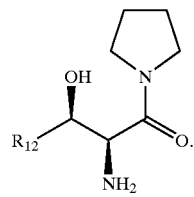

(VII)

$R_{12}$ is a phenyl group substituted with —OCH$_2$CH$_2$O—, halo, —OH, (lower alkyl), lower alkyl thiol, —O(phenyl), —OCH$_2$-(phenyl), lower alkyl, amino, lower alkyl amino and lower dialkyl amino. In a preferred embodiment, the compound is Intermediate (4) depicted in FIG. 1.

Also included in the present invention is the enantiomer of the compound represented by Structural Formula (VI) or (VII), mixtures of the compound and its enantiomer (including racemic mixtures), salts of each enantiomer and mixtures of salts of each enantiomer.

The reactions described above can be combined, resulting in an efficient and highly diastereoselective total synthesis of ceramide-like compounds. The compositions formed by each reaction is a racemic mixture. The ceramide-like enantiomers can be separated or resolved by standard methods of enantiomer separation known to one of ordinary skill in the art, thereby resulting in the preparation of an enantionmerically pure ceramide-like compound. Alternatively, an enantiomerically pure ceramide-like compound can be prepared by separating the enantiomers of the first, second or third racemic mixture and then completing the total synthesis with one or the other pure enantiomer from the first, second or third racemic mixture. Thus, the present invention contemplates performing each reaction with a racemic mixture or, alternatively, with an optically pure stereoisomer. The reactions depicted herein can alternatively be carried out with pure enantiomer or substantially pure enantiomer to yield an optically pure or substantially optically pure product.

DETAILED DESCRIPTION OF THE INVENTION

Figure 1:
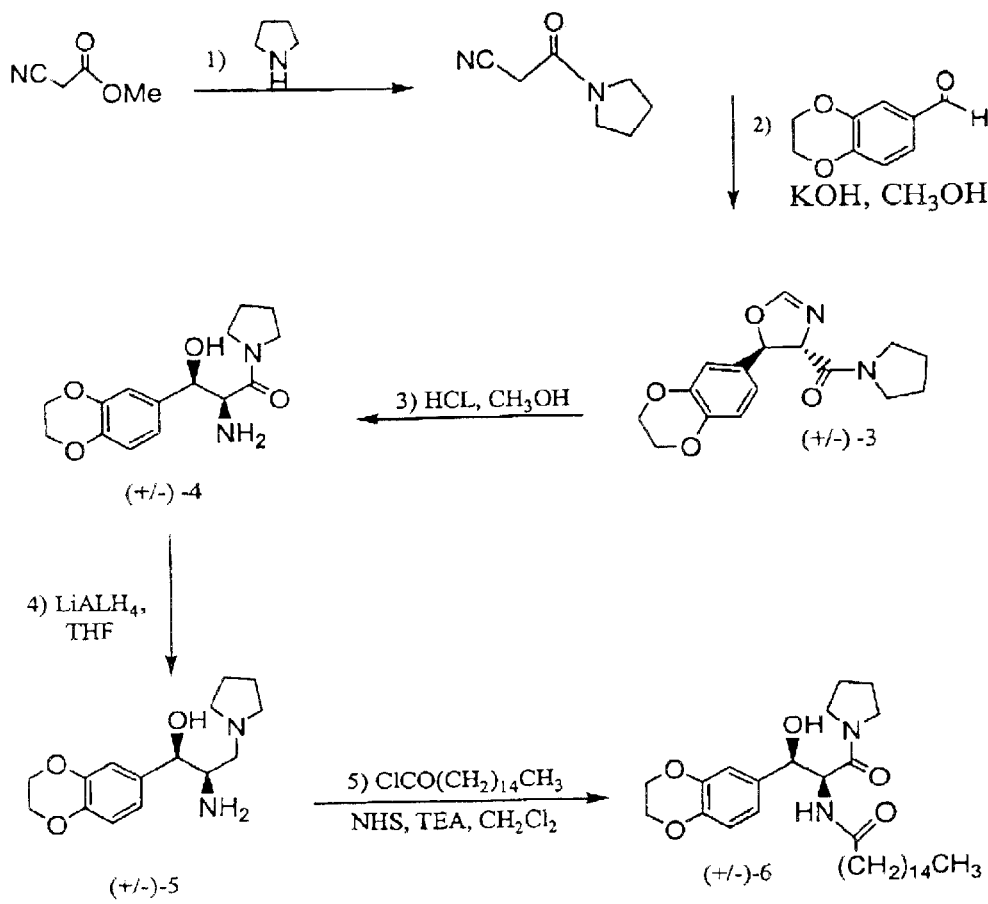
FIG. 1 is a schematic showing the synthesis of ceramide-like compound (6) using the methods disclosed herein.

Described herein is a five step diastereoselective synthesis of ceramide-like compounds from known starting materials. The synthesis begins by preparing an isonitrile compound represented by Structural Formula (II) from the reaction of pyrrolidine with an alkyl ester of isocyanoacetate. The next step in the synthesis is the reaction of an isonitrile compound represented by Structural Formula (II) with the aldehyde $R_{10}$CHO to form a first racemic mixture of enantiomers comprising an oxazoline group. One enantiomer of the first racemic mixture is represented by Structural Formula (I). The oxazoline group in the enantiomers of the first racemic mixture is then hydrolyzed to form a second racemic mixture. One enantiomer of the second racemic mixture is represented by Structural Formula (III). By reacting the second racemic mixture with an amide reducing agent, a third racemic mixture is prepared. One enantiomer of the third racemic mixture is represented by Structural Formula (IV). A racemic mixture of ceramide-like compounds is prepared by acylating the free primary amine group of the enantiomers in the third racemic mixture. The diastereomeric excess of the ceramide-like compounds is generally greater than 99.0% and the overall yield is generally greater than 15%. A pure enantiomer of the ceramide-like compounds can be obtained by separation of the ceramide-like enantiomers using standard methods of resolving enantiomeric mixtures known to one of ordinary skill in the art. Alternatively, the first, second or third enantiomeric mixture can be resolved, i.e., the enantiomers separated, and the total synthesis completed using a pure enantiomer rather than a racemic mixture. This synthesis is shown schematically in FIG. 1. A detailed description of each reaction in the synthesis is provided below.

The isonitrile compound is prepared by reacting a suitable amine such as pyrrolidine with methyl isocyanoacetate (or other lower alkyl ester of isocyanoacetate). Generally, the amine base is used in excess, typically a 50–100% excess. The reaction is normally carried out at 0° C., however, temperatures ranging between about −20° C. to about 80° C. also be used. Conveniently, the reaction can be carried out neat, however solvents that are inert to the reagents can also be used with reagent concentrations typically greater than 1.0 M. Examples include hydrocarbon solvents (e.g., hexane, heptane and benzene) and halogenated solvents (e.g., methylene chloride, chloroform and dichloroethane) and mixtures thereof. Excess amine base is easily removed by azeotropic evaporation with methylene chloride/hexane. The crude product can be used without further purification. Examples of specific conditions for preparing the isonitrile compound are provided in Example 1.

To prepare the first enantiomeric mixture, the isonitrile compound and aldehyde $R_{10}CHO$ are reacted in the presence of a base. Roughly equimolar amounts of these three reagents are generally used. Preferably, a small excess of aldehyde and base are used relative to the isonitrile compound, typically up to about 20%, more typically up to about 10%. Suitable bases are those which can deprotonate a methylene group alpha to an ester group and an isonitrile group without substantially reacting with an aldehdye, ester or isonitrile functional group. Examples include hydroxide and alkoxide bases (potassium, lithium, sodium and the like) and hydride bases (sodium hydride, potassium hydride and the like). Suitable solvents are those which dissolve but do not substantially react with the reagents. Examples include alcoholic solvents such as methanol, ethanol or isopropanol. When hydride bases are used, polar, aprotic solvents such as dimethyl sulfoxide, dimethylformamide and the like are preferred. The reaction is preferably carried out at about 0° C., but can also be carried out at temperatures within the range of about −20° C. to room temperature. Reagent concentrations are typically between about 0.01 M and about 5.0 M, preferably between about 0.1 M and about 1.0 M. Examples of specific conditions for preparing the first racemic mixture are provided in Example 2.

The oxazoline group in the enantiomers of the first racemic mixture can be hydrolyzed with a suitable mineral acid or an organic acid of comparable strength. Examples include hydrochloric acid, sulfuric acid, nitric acid, phosphoric acid and sulfonic acids. The hydrolysis is carried out in water, alcoholic solvents such as methanol, ethanol and isopropanol or mixtures thereof, tetrahydrofuran, acetonitrile, and the like. Suitable reaction temperatures depends upon the strength and concentration of the acid. For example, acid concentrations between about 0.05 M and about 5.0 M and reaction temperatures between about room temperature and about 100° C. can be used when hydrolyzing with hydrochloric acid. Preferably the reaction is carried out between about 40° C. and about 60° C. at concentrations between about 0.1 M and about 1.0 M. Relative to the oxazoline enantiomers, between about 1.0 to about 20 equivalents of acid are used, preferably between about 1.25 and about 5.0 equivalents. The ammonium salt of the product is isolated when an excess of acid is used and is also encompassed within the method of the present invention. Examples of specific conditions for preparing the second racemic mixture are provided in Example 3.

An "amide reducing agent" is a reagent which can reduce an amide to an amine. Such reagents are known in the art and are disclosed, for example, in March, "Advanced Organic Chemistry—Reactions, Mechanisms and Structure", Third Edition, John Wiley & Sons, 1985, pages 1099–1100, Brown and Krishnamurthy, Aldrichimica Acta 12:3 (1979) and references cited therein. Examples include lithium aluminum hydride, lithium triethyl borohydride, borane reagents, aluminum hydride, lithium trimethoxy aluminum hydride and triethyloxonium fluoroborate/sodium borohydride. In the method of the present invention, lithium aluminum hydride is the most commonly used amide reducing agent. Although as little as 0.5 equivalents of lithium aluminum hydride relative to amide starting material can be used, it is more common to use an excess, often up to about five equivalents. Preferably, between about 1.5 and about 2.5 equivalents of lithium aluminun hydride are used relative to the amide starting material. Ethereal solvents are typically used for the reduction; examples include diethyl ether, THF, glyme, diglyme and 1,4-dioxane. Suitable concentrations of reducing agent are generally between about 0.1 M and about 5.0 M, more typically between about 0.8 M and about 1.5 M. The reduction is most commonly carried out at ambient temperature, but temperatures between about 0° C. and about 80° C. or 100° C. can also be used. Examples of specific conditions for preparing the third racemic mixture are provided in Example 4.

The enantiomers in the third racemic mixture can be converted to ceramide-like enantiomers by acylating the free amine. Acylations of amine groups are well known in the art and can be carried out, for example, by reacting the amine with an acylating agent $R_7C(O)$—X. $R_7$ is as described above and X is a leaving group that is readily displaced by a primary amine. Conditions for this reaction are described in, for example, in March, "Advanced Organic Chemistry—Reactions, Mechanisms and Structure", Third Edition, John Wiley & Sons, 1985 and references cited therein. Examples of suitable acylating agents include acid halides, anhydrides or esters. Preferably, the amine is acylated with an acid chloride. Generally, equimolar amounts of the compound (or enantiomer) with the free amine and the acid chloride are used in the presence of a small excess, relative to the acid chloride, of a tertiary amine such as triethylamine, diisopropylethylamine, dimethylaminopyridine or pyridine is used. However, an excess of acid chloride (typically about 10–50%) can be used when the compound (or enantiomer) with the free amine is limiting, and vice versa. The concentrations of the reagents in the reaction mixture normally vary between about 0.005 M and about 5.0 M, and are preferably between about 0.05 M and about 0.5 M. The excess of amine base can be greater than about 100%, but is typically between about 5% and about 25%. Aprotic solvents such as halogenated solvents are preferred (e.g., chloroform, methylene chloride and 1,2-dichloromethane), however other aprotic solvents such as ethereal solvents and hydrocarbon solvents can be suitable substitutes. Ambient temperature is normally preferred for the reaction, but temperatures between about 0° C. and about 50° C. can also be used.

Alternatively, the acylating agent is an activated ester $R_7C(O)$—OX', wherein —OX' is readily displaced by a primary amine. Methods of acylating an amine with activated esters are known in the art and are described, for example, in March, "Advanced Organic Chemistry—Reactions, Mechanisms and Structure", Third Edition, John Wiley & Sons, 1985, pages 371–375, and references cited therein. Many activated esters are stable enough to be isolated. N-Hydroxy succinimidyl esters, some of which are commercially available from Aldrich Chemical Co., Milwaukee, Wis., are one example of activated esters of this type. Conditions suitable for forming an amide with an acid chloride acylating agent, described in the prior paragraph, can typically be used with a stable activated ester. In contrast with acid chlorides, which require activation with tertiary amines, activated esters are reactive enough so that they form amides directly in the presence of primary amines. Therefore, the tertiary amine can be omitted from the acylation reaction when activated esters are used.

Alternatively, an activated ester is formed in situ. Formation of an activated ester in situ requires a "coupling agent", which is a reagent that replaces the hydroxyl group of a carboxyl acid with a group which is susceptible to nucleophilic displacement. Examples of coupling agents include 1,1'-carbonyldiimidazole (CDI), isobutyl chloroformate, dimethylaminopropylethyl-carbodiimide (EDC), dicyclohexyl carbodiimide (DCC). When amidating by in situ generation of an activated ester, an excess of either the carboxylic acid or amine can be used (typically a 50% excess, more typically about a 10–15% excess). However, it is more common when carrying out the present invention to use the amine compound as the limiting reagent. Generally, from about 1.0 moles to about 10 moles of coupling agent are used per mole of carboxylic acid, preferably from about 1.0 mole to about 1.5 moles of coupling agent per mole of carboxylic acid. The reaction is generally carried out in aprotic solvents, for example, halogenated solvents such as methylene chloride, dichloroethane and chloroform, ethereal solvents tetrahydrofuran, 1,4-dioxane and diethyl ether and dimethylformamide. Suitable reaction temperature generally range from between about 0° to about 100° C., but the reaction is preferably carried out at ambient temperature.

In a preferred embodiment in Structural Formulas (I)–(V), $R_{10}$ is a substituted phenyl group and $R_{20}$ and $R_{30}$ are independently an unsubstituted C1–C5 alkyl group or, taken together with the nitrogen atom to which they are bonded, are an unsubstituted C3–C10 non-aromatic heterocyclic ring. More preferably, $R_{20}$ and $R_{30}$, taken together with the nitrogen atom to which they are bonded, are a non-aromatic heterocyclic group which has a nitrogen as a ring atom. As used herein, a "non-aromatic heterocyclic group" is a cyclic moiety that contains one or more heteroatoms such as nitrogen, oxygen or sulfur as a ring atom and is non-aromatic. Examples include pyrrolidinyl, piperazinyl, azetidinyl, morpholinyl, thiomorpholinyl, azacycloheptyl, piperidinyl and N-phenylpiperazinyl. A preferred non-aromatic heterocylic group is pyrrolidinyl.

In a more preferred embodiment in Structural Formulas (I)–(V), $R_{10}$ is phenyl group substituted with —OCH$_2$O—, —OCH$_2$CH$_2$O—, halo, —O(lower alkyl), lower alkyl thiol, —OH, —O(phenyl), —OCH$_2$-(phenyl), lower alkyl, amino, lower alkyl amino and lower dialkyl amino; and $R_{20}$ and $R_{30}$, as described in the previous paragraph.

An "aliphatic group" is non-aromatic, consists solely of carbon and hydrogen and may optionally contain one or more units of unsaturation, e.g., double and/or triple bonds. An aliphatic group may be straight chained, branched or cyclic. When straight chained or branched, an aliphatic group typically contains between about 1 and about 30 carbon atoms, more typically between about 1 and about 24 carbon atoms. When cyclic, an aliphatic group typically contains between about 3 and about 10 carbon atoms, more typically between about 3 and about 7 carbon atoms. Aliphatic groups are preferably lower alkyl groups, which include C1–C30 straight chained or branched saturated hydrocarbons, preferably C1–C24 straight chained or branched saturated hydrocarbons. Examples include methyl, ethyl, n-propyl, iso-propyl, n-butyl, sec-butyl and tert-butyl.

Aromatic groups include carbocyclic aromatic groups such as phenyl, 1-naphthyl, 2-naphthyl, 1-anthracyl and 2-anthacyl, and heterocyclic aromatic groups such as N-imidazolyl, 2-imidazole, 2-thienyl, 3-thienyl, 2-furanyl, 3-furanyl, 2-pyridyl, 3-pyridyl, 4-pyridyl, 2-pyrimidy, 4-pyrimidyl, 2-pyranyl, 3-pyranyl, 3-pyrazolyl, 4-pyrazolyl, 5-pyrazolyl, 2-pyrazinyl, 2-thiazole, 4-thiazole, 5-thiazole, 2-oxazolyl, 4-oxazolyl and 5-oxazolyl.

Aromatic groups also include fused polycyclic aromatic ring systems in which a carbocyclic aromatic ring or heteroaryl ring is fused to one or more other heteroaryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl and 3-isoindolyl.

Suitable substituents on a lower alkyl, aliphatic, aromatic, non-aromatic heterocyclic or benzyl group are those which do not substantially interfere with the reactions described herein. "Interfering with a reaction" refers to substantially decreasing the yield (e.g., a decrease of greater than 50%) or causing a substantial amount of by-product formation (e.g., where by-products comprise at least 50% of the theoretical yield). Interfering substituents can be used, provided that they are first converted to a protected form. Suitable protecting groups are known in the art and are disclosed, for example, in Greene and Wuts, "Protective Groups in Organic Synthesis", John Wiley & Sons (1991).

Suitable substituents on an alkyl, aliphatic, aromatic, non-aromatic heterocyclic ring or benzyl group include, for example, halogen (—Br, —Cl, —I and —F) —OR, —NO$_2$, —NR$_2$ and —SO$_k$R (k is 0, 1 or 2). Each R is independently —H, an aliphatic group, a substituted aliphatic group, a benzyl group, a substituted benzyl group, an aromatic group or a substituted aromatic group, and preferably —H, a lower alkyl group, a benzylic group or a phenyl group. Preferably, each R is —H, a lower alkyl group, a benzylic group or an aromatic group. A substituted non-aromatic heterocyclic ring, benzylic group or aromatic group can also have an aliphatic or substituted aliphatic group as a substituent. A substituted alkyl or aliphatic group can also have a non-aromatic heterocyclic ring, benzyl, substituted benzyl, aromatic or substituted aromatic group as a substituent. A substituted alkyl, substituted aliphatic, substituted non-aromatic heterocyclic, substituted aromatic or substituted benzyl group can have more than one substituent.

Compounds and enantiomers of this invention such as compounds and enantiomers represented by Structural Formulas (I) and (III)–(VII) possess a sufficiently basic group which can react with any of a number of inorganic and organic acids to form a salt. Thus, the present invention also includes salts of the compounds and enantiomers represented by Structural Formulas (I), (III)–(VII). In particular, a salt of the compound or enantiomer represented by Structural Formula (III) is formed when an excess of acid is used to hydrolyze the oxazoline group of the enantiomer or compound of Structural Formula (I). The use of an excess of acid and formation of the salt is encompassed within the method of the present invention. Physiologically acceptable salts are preferred. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Standard methods known to one or ordinary skill in the art that are used to resolve or separate optical isomers, one from the other, can be utilized to separate the enantiomers in the first, second, third or fourth racemic mixture. For example, enantiomers are commonly separated by high pressure liquid chromatography using chiral columns. For example, ceramide-like enantiomers can be separated using CHIREX (S)-VAL and (R)-NE columns, as described in Example 5. The intermediates prepared in Examples 3 and 4 can be separated on Chiral PAK AD—Amylose Tris (3,5-Dimethylphenylcarbanate Columns (Chiral Technologies, Inc.). Another more common method of optical isomer resolution is to convert the racemic mixture to a mixture of diastereomers which can then be separated by crystallization, chromatography and the like, followed by conversion back to the desired enantiomer. Resolution techniques which can be used also include triage, formation and separation of diasteromeric salts, esters, amides or other chemical derivatives, kinetic resolution via enzymes or chemical catalysis and chiral chromatography, including simulated moving bed methods.

The method of preparing ceramide-like compounds described herein is a diastereoselective synthesis that involves the formation of racemic mixtures. The desired enantiomer is obtained from one of the racemic mixtures by standard methods of separating optical isomers from racemic mixtures, as described in the previous paragraph. Although a chiral inducing agent can be used, in most instances as in the reactions disclosed herein and, in particular the reaction of $R_{10}CHO$ and the compound represented by Structural Formula (I), the reaction is carried out in the absence of a chiral inducing agent. A "chiral inducing agent" is an agent added to a reaction mixture that results in the formation of one enantiomer in preference to the other. Chiral inducing agents are generally optically active. Examples of chiral inducing agents which can be used to prepare enantiomerically enriched mixtures of oxazoline compounds include the chiral ferrocenyl-phosphine ligands disclosed in, for example, Ito et al., *Tetrahedron Letters* 29:6324 (1988).

The entire teachings of the publications cited in this application are incorporated herein by reference.

EXEMPLIFICATION

Example 1

1-(Isocyano-Acetyl)-Pyrrolidine

To a stirred and cooled (0° C.) methyl isocyanoacetate (technical grade, 95%; 5.00 g, 47.8 mmol) was slowly added pyrrolidine (6.5 ml, 78 mmol). The mixture was stirred overnight with continued cooling and then concentrated. The resulting oil was repeatedly coevaporated from methylene chloride/hexane to remove residual pyrrolidine. Crude product, which was used in the next step without further purification, was thus afforded as 6.35 g (96%) of dark brown oil: $^1$H NMR (CDCl$_3$) δ 4.24 (s, 2H), 3.53 (t, J=6.8, 2H), 3.41 (t, J=6.8, 2H), 2.02 (quintet, J=6.8, 2H), 1.90 (quintet, J=6.8, 2H) ppm.

Example 2

(±)-Trans-[5-(2,3-Dihydro-Benzo[1,4]Dioxin-6-yl)-4,5-Dihydro-Oxazol-4-yl]-Pyrrolidin-1-yl-Methanone To a stirred and cooled (0° C.) solution of potassium hydroxide (2.70 g, 48.1 mmol) in methanol (30 ml) was added a mixture of 1,4-benzodioxan-6-carboxaldehyde (8.20 g, 50.0 mmol) and the product from Example 1 (6.30 g, 45.6 mmol). The solution was stirred overnight with continued cooling and then concentrated. The residue was partitioned between ethyl acetate and water. The organic layer was combined with additional ethyl acetate extracts, washed with aqueous sodium chloride and dried (magnesium sulfate). Concentration afforded crude product as a golden, glassy solid. Flash chromatography over silica (ethyl acetate) yielded 9.40 g (68%) of product as a colorless glassy solid. $^1$H NMR (CDCl$_3$) δ 6.99 (s, 1H), 6.90–6.78 (m, 3H), 6.00 (d, J=7.3, 1H), 4.58, (d, J=7.3, 1H), 4.26 (s, 4H), 3.95–3.87 (m, 1H), 3.55–3.41 (m, 3H), 2.04–1.80 (m, 4H) ppm.

Example 3

(±)-Threo-2-Amino-3-(2,3-Dihydro-Benzo[1,4]Dioxin-6-yl)-3-Hydroxy-1-Pyrrolidin-1-yl-Propan-1-One Hydrochloride To a solution of the product from Example 2 (3.94 g, 13.0 mmol) in methanol was added hydrochloric acid (2.2 ml). After heating (50° C.) the mixture for 3 hours, more hydrochloric acid (1.0 ml) was added and heating was continued for an additional 45 minutes. The reaction was then concentrated and the resulting yellow oil was coevaporated twice with ethyl acetate before solidifying. Trituration (ethyl acetate) and vacuum oven drying afforded 3.78 g (88%) of product as a bright yellow solid. $^1$H NMR (CD$_3$OD) δ 6.90–6.82 (m, 3H), 4.73 (d, J=9.2, 1H), 4.23 (s, 4H), 4.04 (d, J=9.2, 1H), 3.42–3.18 (m, 3H), 2.35–2.24 (m, 1H), 1.83–1.67 (m, 2H), 1.67–1.43 (m, 2H) ppm.

Example 4

(±)-Threo-2-Amino-1-(2,3-Dihydro-Benzo[1,4]Dioxin-6-yl)-3-Pyrrolidin-1-yl-Propan-1-ol To a stirred suspension of the product of Example 3 (2.00 g, 6.08 mmol) in tetrahydrofuran (250 ml) was slowly added, in two portions, lithium aluminum hydride (1.43 g, 37.7 mmol). The mixture was stirred overnight and then quenched by the slow, dropwise addition of water (approximately 50 ml). The white suspension was then concentrated to remove tetrahydrofuran and taken back up in a mixture of methylene chloride (300 ml) and 1 N aqueous hydrochloric acid (50 ml). The aqueous layer was basified to pH 10–11 by the slow addition of 1 N aqueous sodium hydroxide. The organic layer was removed, combined with additional methylene chloride extracts and dried (sodium sulfate). Concentration afforded crude product as a yellow oil. This material was purified by flash chromatography over silica gel with chloroform/methanol/ammonium hydroxide to furnish 1.15 g (68%) of product as a near colorless gum: $^1$H NMR (CDCl$_3$) δ 6.89–6.76 (m, 3H), 4.54 (d, J=3.7, 1H), 4.25 (s, 4H), 3.14–3.07 (m, 1H), 2.68–2.41 (m, 6H), 1.82–1.71 (m, 4H) ppm.

Example 5

(±)-Threo-Hexadeconic Acid-[2-(2,3-Dihydro-Benzo[1,4]Dioxin-6-yl)-2-Hydroxy-1-Pyrrolidin-1-ylmethyl-Ethyl]Amide To a stirred solution of the product of Example 4 (0.158 g, 0.568 mmol) in methylene chloride (10 ml) was added, in order, N-hydroxysuccinimide (0.068 g, 0.591 mmol), triethylamine (95 μl, 0.68 mmol) and palmitoyl chloride (155 μl, 0.511 mmol) The mixture was stirred for 2.5 hours and then partitioned between methylene chloride and 1 N aqueous sodium hydroxide. The organic layer was dried (sodium sulfate) and concentrated. The resulting white solid was flash chromatographed over silica gel with (chloroform/methanol) to afford 0.109 g (41%) of product as a white solid. Analytical chiral HPLC (column: Chirex (S)-VAL and (R)-NE, 4.6×250 mm, eluant: 0.5% trifluoroacetic acid in 67:31:2 hexane/methylene chloride/ethanol; flow; 1 ml/min; detection: 280 nM) determined the diastereomeric purity of the product to be 99.3% (i.e., total contamination by the two erythro enantiomers is 0.7%). $^1$H NMR (CDCl$_3$) δ 6.88–6.73 (m, 3H), 5.84 (d, J=3.8, 1H), 4.24 (s, 4H), 4.22–4.15 (m, 1H), 2.86–2.72 (m, 2H), 2.72–2.55 (m, 4H), 2.10 (t, J=7.5, 2H), 1.82–1.74 (m, 4H), 1.58–1.46 (m, 2H), 1.32–1.16 (m, 24H), 0.88 (t, J=6.7, 3H) ppm.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preparing a composition comprising a compound represented Structural Formula (I):

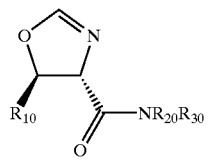

(I)

wherein:
R$_{10}$ is a substituted aromatic group, provided that when R$_{20}$ and R$_{30}$ are both —H, then R$_{10}$ is not 4-nitrophenyl; and
R$_{20}$ and R$_{30}$ are independently —H, a substituted or unsubstituted aliphatic group or, taken together with the nitrogen atom to which they are bonded, are a substituted or unsubstituted non-aromatic heterocyclic ring;
said method comprising the step of reacting an aldehyde compound R$_{10}$CHO with an isonitrile compound represented by Structural Formula (II):

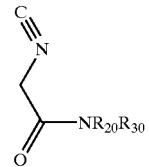

(II)

said method being carried out in the absence of a chiral inducing agent.

2. The method of claim 1 wherein R$_{20}$ and R$_{30}$ are independently an unsubstituted C1–C5 alkyl group or, taken together with the nitrogen atom to which they are bonded, are an unsubstituted C3–C10 non-aromatic heterocyclic ring and R$_{10}$ is a substituted phenyl group.

3. The method of claim 2 wherein R$_{20}$ and R$_{30}$, taken together with the nitrogen atom to which they are bonded, are pyrrolidinyl, piperazinyl, azetidinyl, morpholinyl, thiomorpholinyl, azacycloheptyl, piperidinyl or N-phenylpiperazinyl.

4. The method of claim 1, wherein the composition is a racemic mixture comprising the compound represented by Structural Formula (I) and its enantiomer, and wherein the method further comprises the steps of:
a) resolving the compound represented by Structural Formula (I) from its enantiomer; and
b) hydrolyzing the oxazoline group of the resolved compound to form a compound represented by Structural Formula (III):

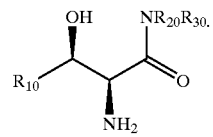

(III)

5. A method of the of claim 2 wherein R$_{20}$ and R$_{30}$, taken together with the nitrogen atom to which they are bonded, are a pyrrolidinyl group.

6. The method of claim 5 wherein R$_{10}$ is phenyl group substituted with —OCH$_2$O—, —OCH$_2$CH$_2$O—, halo, —O(lower alkyl), lower alkyl thiol, —OH, —O(phenyl), —O—CH$_2$(phenyl), lower alkyl, amino, lower alkyl amino or lower dialkyl amino.

7. A method of preparing a composition comprising a compound represented by Structural Formula (III):

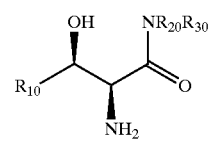

(III)

wherein:
R$_{10}$ is a substituted or unsubstituted aromatic group, provided that when R$_{20}$ and R$_{30}$ are both —H, then R$_{10}$ is not 3-pyridyl, phenyl or 4-nitrophenyl; and
R$_{20}$ and R$_{30}$ are independently —H, a substituted or unsubstituted aliphatic group or, taken together with the nitrogen atom to which they are bonded, are a substituted or unsubstituted non-aromatic heterocyclic ring; comprising the step of reacting an aldehyde compound R$_{10}$CHO with an isonitrile compound represented by Structural Formula (II):

(II)

thereby forming an intermediate represented by Structural Formula (I):

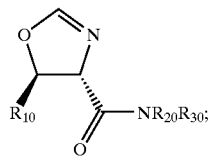

(I)

hydrolyzing the oxazoline group in the compound represented by Structural Formula (I), thereby forming the compound represented by Structural Formula (III).

8. The method of claim 7, further comprising the step of isolating the compound represented by structural Formula (I) before hydrolyzing the oxazoline group.

9. The method of claim 7 wherein the second composition is a racemic mixture comprising the compound represented by Structural Formula (III) and it enantiomer, and wherein the method further comprises the steps of:

a) resolving the compound represented by Structural Formula (III) from its enantiomer; and b) reacting the resolved compound with an amide reducing agent to form a compound represented by Structural Formula (IV):

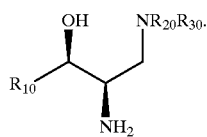

(IV)

10. The method of claim 7 wherein $R_{20}$ and $R_{30}$, taken together with the nitrogen atom to which they are bonded, are pyrrolidinyl, piperazinyl, azetidinyl, morpholinyl, thiomorpholinyl, azacycloheptyl, piperidinyl or N-phenylpiperazinyl.

11. The method of the of claim 10 wherein:

a) $R_{20}$ and $R_{30}$, taken together with the nitrogen atom to which they are bonded, are a pyrrolidinyl group; and b) $R_{10}$ is a phenyl group substituted with —OCH$_2$O—, —OCH$_2$CH$_2$O—, halo, —O(lower alkyl), lower alkyl thiol, —OH, —O(phenyl), —OCH$_2$—(phenyl), lower alkyl, amino, lower alkyl amino and lower dialkyl amino.

12. The method of claim 7 further comprising the step of reacting the compound represented by Structural Formula (III) with an amide reducing agent, thereby forming a third composition comprising a compound represented by Structural Formula (IV):

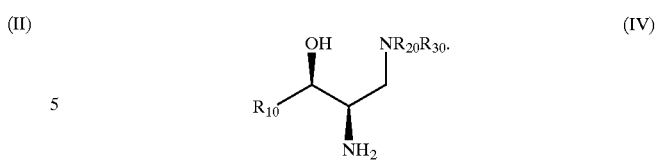

(IV)

13. The method of claim 12 wherein the third composition is a racemic mixture comprising the compound represented by Structural Formula (IV) and its enantiomer, and wherein the method further comprises the steps of:

a) resolving the compound represented by Structural Formula (IV) from its enantiomer; and b) acylating the primary amine group of the resolved compound, thereby forming a fourth composition comprising a compound represented by Structural Formula (V):

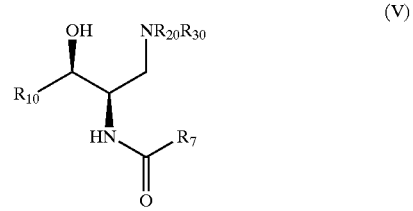

(V)

wherein $R_7$ is an aliphatic group.

14. The method of claim 13 wherein the fourth composition is a racemic mixture of the compound represented by Structural Formula (V) and its enantiomer and wherein the method further comprises the step of resolving the compound represented by Structural Formula (V) from its enantiomer.

15. The method of claim 12 wherein the amide reducing agent is lithium aluminum hydride.

16. The method of claim 15 wherein $R_{20}$ and $R_{30}$, taken together with the nitrogen atom to which they are bonded, are pyrrolidinyl, piperazinyl, azetidinyl, morpholinyl, thiomorpholinyl, azacycloheptyl, piperidinyl or N-phenylpiperazinyl.

17. The method of the of claim 16 wherein:

a) $R_{20}$ and $R_{30}$, taken together with the nitrogen atom to which they are bonded, are a pyrrolidinyl group; and b) $R_{10}$ is a phenyl group substituted with —OCH$_2$O—, —OCH$_2$CH$_2$O—, halo, —O(lower alkyl), lower alkyl thiol, —OH, —O(phenyl), —OCH$_2$-(phenyl), lower alkyl, amino, lower alkyl amino and lower dialkyl amino.

18. The method of claim 12, further comprising the step of acylating the compound represented by Structural Formula (IV), thereby forming a fourth composition comprising a compound represented by Structural Formula (V):

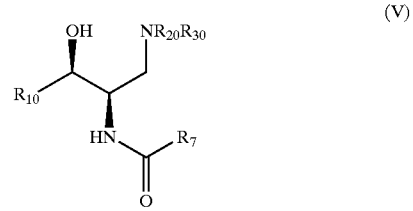

(V)

wherein $R_7$ is an aliphatic group.

19. The method of claim 18 wherein the compound represented by Structural Formula (IV) is acylated with $R_7COX$, wherein is X is —Cl or an —O—N-succinimidyl group and $R_7$ is a $C_1$–$C_{30}$ straight chained alkyl or alkenyl group.

20. The method of claim 19 wherein $R_{20}$ and $R_{30}$, taken together with the nitrogen atom to which they are bonded, are pyrrolidinyl, piperazinyl, azetidinyl, morpholinyl, thiomorpholinyl, azacycloheptyl, piperidinyl or N-phenylpiperazinyl.

21. The method of the of claim 20 wherein:
    a) $R_{20}$ and $R_{30}$, taken together with the nitrogen atom to which they are bonded, are a pyrrolidinyl group;
    b) $R_{10}$ is a phenyl group substituted with —OCH$_2$O—, —OCH$_2$CH$_2$O—, halo, —O(lower alkyl), lower alkyl thiol, —OH, —O(phenyl), —O—CH$_2$-(phenyl), lower alkyl, amino, lower alkyl amino and lower dialkyl amino; and
    c) and $R_7$ is a $C_{10}$–$C_{16}$ alkyl group.

22. A method of preparing a product composition comprising a compound represented by Structural Formula (IV):

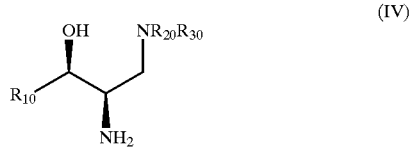

(IV)

wherein:

$R_{10}$ is a substituted or unsubstituted aromatic group; and
$R_{20}$ and $R_{30}$ are independently —H, a substituted or unsubstituted aliphatic group or, taken together with the nitrogen atom to which they are bonded, are a substituted or unsubstituted non-aromatic heterocyclic ring;

said method comprising the step of reacting a starting composition with an amide reducing agent, thereby forming the product composition, wherein the starting composition comprises a compound represented by Structural Formula (III):

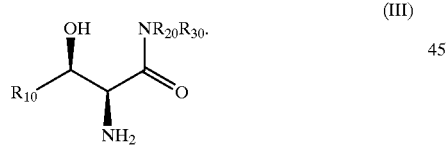

(III)

23. The method of claim 22 wherein the amide reducing agent is lithium aluminum hydride.

24. The method of claim 22 wherein $R_{20}$ and $R_{30}$, taken together with the nitrogen atom to which they are bonded, are pyrrolidinyl, piperazinyl, azetidinyl, morpholinyl, thiomorpholinyl, azacycloheptyl, piperidinyl or N-phenylpiperazinyl.

25. The method of the of claim 22 wherein:
    a) $R_{20}$ and $R_{30}$, taken together with the nitrogen atom to which they are bonded, are a pyrrolidinyl group; and
    b) $R_{10}$ is a phenyl group substituted with —OCH$_2$O—, —OCH$_2$CH$_2$O—, halo, —O(lower alkyl), lower alkyl thiol, —OH, —O(phenyl), —OCH$_2$-(phenyl), lower alkyl, amino, lower alkyl amino and lower dialkyl amino.

26. The method of claim 22 wherein the composition is a racemic mixture comprising the compound represented by Structural Formula (IV) and its enantiomer and wherein the method further comprises the step of resolving the compound represented by Structural Formula (IV) from its enantiomer.

27. A method of preparing a composition comprising a first compound represented by the following structural formula:

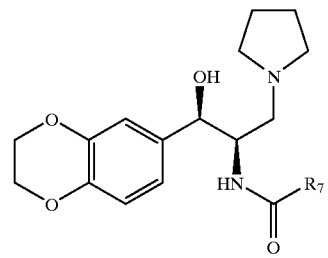

wherein $R_7$ is a $C_8$–$C_{18}$ alkyl group;

said method comprising the steps of:

a) reacting an aldehyde compound represented by the following structural formula:

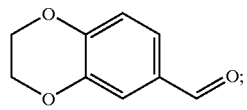

with an isonitrile compound represented by the following structural formula:

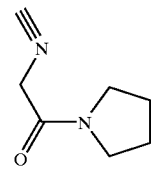

thereby forming a composition comprising a heterocyclic compound represented by the following structural formula:

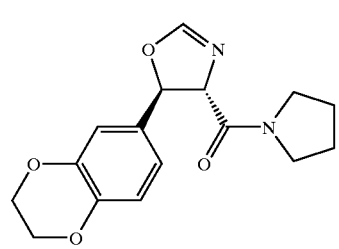

(III)

b) hydrolyzing the oxazoline group in the heterocyclic compound formed in step a), thereby forming a composition comprising an amide compound represented by the following structural formula:

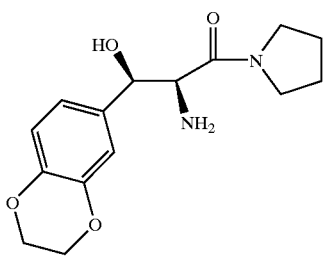

c) reacting the amide compound formed in step b) with lithium aluminum hydride, thereby forming a composition comprising a cyclic amine compound represented by the following structural formula:

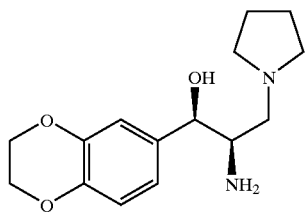

d) and acylating the primary amine group in the cyclic amine compound formed in step c) with R$_7$COX, wherein is X is —Cl or an —O—N-succinimidyl group and R$_7$ is a C$_8$–C$_{18}$ straight chained alkyl group, thereby forming the composition comprising the first compound.

28. The method of claim 27, wherein the composition formed in step a) is a racemic mixture comprising the heterocyclic compound and its enantiomer and wherein the heterocyclic compound is separated from its enantiomer before reacting the heterocyclic compound in step b).

29. The method of claim 27, wherein the composition formed in step b) is a racemic mixture comprising the amide compound and its enantiomer and wherein the amide compound is separated from its enantiomer before reacting the amide compound in step c).

30. The method of claim 27, wherein the composition formed in step c) is a racemic mixture comprising the cyclic amine compound and its enantiomer and wherein the cyclic amine compound is separated from its enantiomer before reacting the cyclic amine compound in step d).

31. The method of claim 27, wherein the composition formed in step d) is a racemic mixture comprising the ceramide-like compound and its enantiomer and wherein the first compound is separated from its enantiomer.

32. The method of claim 27 wherein R$_7$ is a C15 alkyl group.

33. A method of preparing a composition comprising a compound represented by Structural Formula (I):

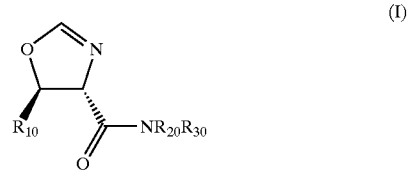

(I)

wherein:

R$_{10}$ is a substituted or unsubstituted 1-naphthyl, 2-naphthyl, 1-anthracyl and 2-anthacyl, and heterocyclic aromatic groups such as N-imidazolyl, 2-imidazole, 2-thienyl, 3-thienyl, 2-furanyl, 3-furanyl, 2-pyridyl, 3-pyridyl, 4-pyridyl, 2-pyrimidy, 4-pyrimidyl, 2-pyranyl, 3-pyranyl, 3-pyrazolyl, 4-pyrazolyl, 5-pyrazolyl, 2-pyrazinyl, 2-thiazole, 4-thiazole, 5-thiazole, 2-oxazolyl, 4-oxazolyl or 5-oxazolyl, or R$_{10}$ is a substituted phenyl, provided that when R$_{20}$ and R$_{30}$ are both —H, then R$_{10}$ is not 3-pyridyl or 4-nitrophenyl; and R$_{20}$ and R$_{30}$ are independently —H, a substituted or unsubstituted aliphatic group or, taken together with the nitrogen atom to which they are bonded, are a substituted or unsubstituted non-aromatic heterocyclic ring;

said method comprising the step of reacting an aldehyde compound R$_{10}$CHO with an isonitrile compound represented by Structural Formula (II):

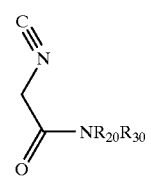

(II)

said method being carried out in the absence of a chiral inducing agent.

* * * * *